(12) United States Patent
Garnier et al.

(10) Patent No.: US 12,012,230 B2
(45) Date of Patent: Jun. 18, 2024

(54) DEVICE AND METHOD FOR EMPTYING AND MONITORING FLUID DRAINED FROM AN ENGINE OF AN AIRCRAFT

(71) Applicant: SAFRAN AIRCRAFT ENGINES, Paris (FR)

(72) Inventors: Alméric Pierre Louis Garnier, Moissy-cramayel (FR); Josselin Xavier Coupard, Moissy-cramayel (FR)

(73) Assignee: SAFRAN AIRCRAFT ENGINES, Paris (FR)

( * ) Notice: Subject to any disclaimer, the term of this patent is extended or adjusted under 35 U.S.C. 154(b) by 782 days.

(21) Appl. No.: 17/251,409

(22) PCT Filed: Jun. 7, 2019

(86) PCT No.: PCT/FR2019/051392
§ 371 (c)(1),
(2) Date: Dec. 11, 2020

(87) PCT Pub. No.: WO2019/239047
PCT Pub. Date: Dec. 19, 2019

(65) Prior Publication Data
US 2021/0253274 A1    Aug. 19, 2021

(30) Foreign Application Priority Data
Jun. 14, 2018  (FR) ...................................... 1855222

(51) Int. Cl.
*B64F 5/40*     (2017.01)
*B64C 1/14*     (2006.01)
(Continued)

(52) U.S. Cl.
CPC .............. *B64F 5/40* (2017.01); *B64C 1/1453* (2013.01); *G01N 33/2888* (2013.01);
(Continued)

(58) Field of Classification Search
CPC ..... B64F 5/40; B64C 1/1453; G01N 33/2888; F01M 11/10; F16N 2200/00;
(Continued)

(56) References Cited

U.S. PATENT DOCUMENTS

| | | |
|---|---|---|
| 5,452,695 A | 9/1995 | Bedi |
| 5,610,341 A | 3/1997 | Tortora |

(Continued)

FOREIGN PATENT DOCUMENTS

| | | |
|---|---|---|
| WO | 9315309 A1 | 8/1993 |
| WO | WO 2015/082833 A1 | 6/2015 |

OTHER PUBLICATIONS

Search Report dated Feb. 11, 2019, in FR Application No. 1855222 (2 pages).

(Continued)

*Primary Examiner* — Jason K Niesz
(74) *Attorney, Agent, or Firm* — Bookoff McAndrews, PLLC

(57) ABSTRACT

The invention relates to the field of aeronautical propulsion, and more specifically to an emptying and monitoring device and method for emptying and monitoring a fluid drained from an aircraft engine. The emptying and monitoring device comprises at least one first intake passage for receiving, directly from the aircraft, fluid drained from the engine, and a first quality sensor assembly for detecting at least one quality parameter of the fluid drained from the engine, having been admitted through the first intake passage.

14 Claims, 3 Drawing Sheets

(51) Int. Cl.
*G01N 33/28* (2006.01)
*G05D 1/00* (2006.01)
*F01M 11/04* (2006.01)
*F01M 11/10* (2006.01)
*F16N 31/00* (2006.01)

(52) U.S. Cl.
CPC ....... *G05D 1/0088* (2013.01); *F01M 11/0458* (2013.01); *F01M 11/10* (2013.01); *F16N 31/004* (2013.01); *F16N 2200/00* (2013.01); *F16N 2200/04* (2013.01); *F16N 2200/12* (2013.01); *F16N 2210/02* (2013.01); *F16N 2250/18* (2013.01); *F16N 2250/36* (2013.01)

(58) Field of Classification Search
CPC ............ F16N 2200/04; F16N 2200/12; F16N 2210/02; F16N 2250/18
See application file for complete search history.

(56) References Cited

U.S. PATENT DOCUMENTS

| | | | |
|---|---|---|---|
| 5,893,398 A | 4/1999 | Garrett, Jr. | |
| 6,782,665 B2 * | 8/2004 | Fahrion | B64F 5/40 |
| | | | 182/36 |
| 6,860,300 B1 * | 3/2005 | Kuntz | B64F 1/28 |
| | | | 141/98 |
| 7,213,621 B1 * | 5/2007 | Chang | F16N 31/00 |
| | | | 141/297 |
| 8,740,251 B2 * | 6/2014 | Batson | B64F 1/28 |
| | | | 137/355.19 |
| 2002/0148788 A1 | 10/2002 | Berns et al. | |
| 2004/0060344 A1 | 4/2004 | Kauffman et al. | |
| 2004/0165185 A1 | 8/2004 | Reintjes et al. | |
| 2012/0210769 A1 | 8/2012 | Roper | |
| 2015/0343346 A1 | 12/2015 | Sheridan | |
| 2017/0008647 A1 * | 1/2017 | Pountney | G01M 17/007 |
| 2017/0089236 A1 | 3/2017 | Andersen et al. | |
| 2018/0229860 A1 * | 8/2018 | Clermont | B64F 1/228 |

OTHER PUBLICATIONS

International Search Report issued in International Application No. PCT/FR2019/051392 mailed Nov. 20, 2019 (2 pages).

\* cited by examiner

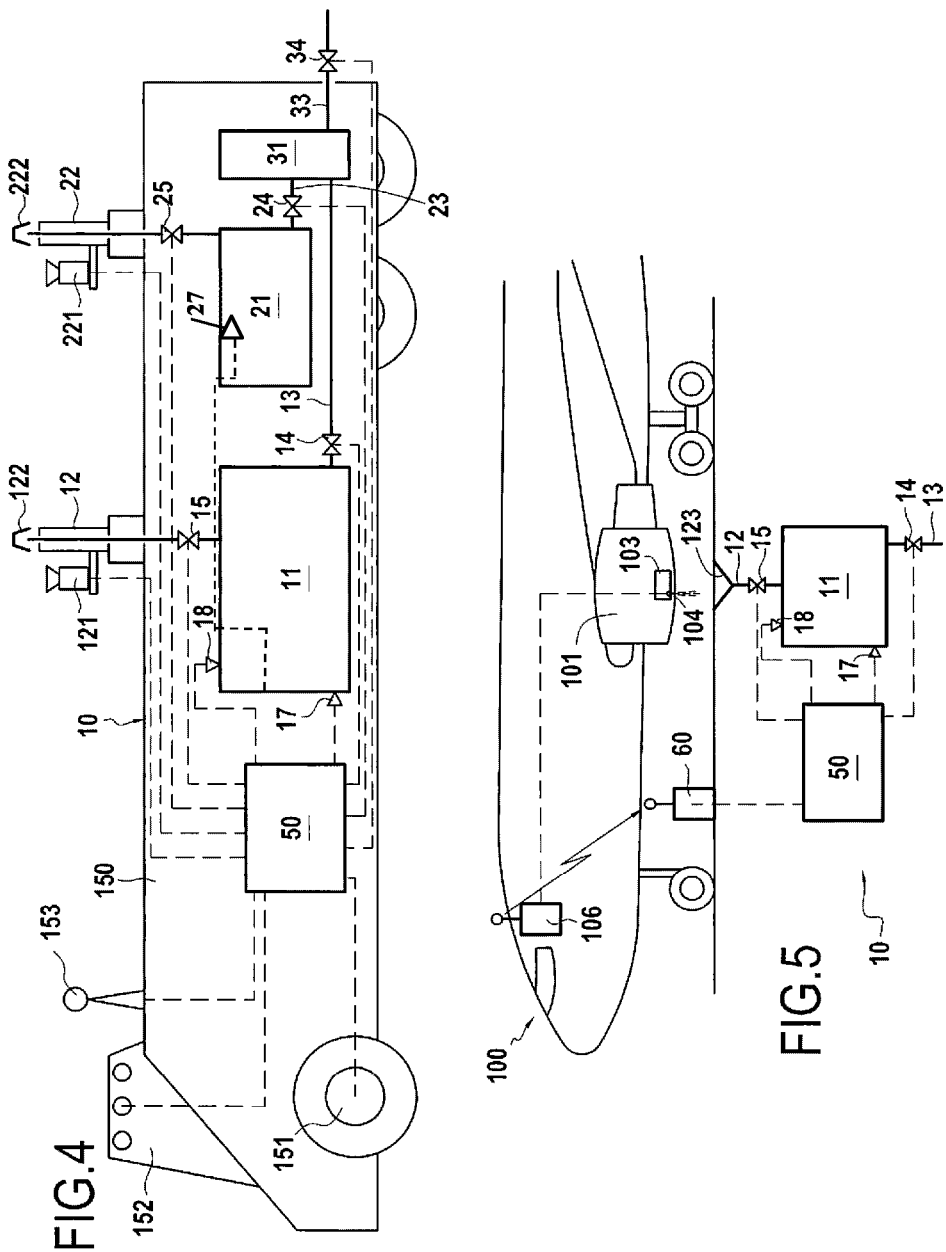

DEVICE AND METHOD FOR EMPTYING AND MONITORING FLUID DRAINED FROM AN ENGINE OF AN AIRCRAFT

CROSS-REFERENCE TO RELATED APPLICATION(S)

This application is the U.S. national phase entry under 35 U.S.C. § 371 of International Application No. PCT/FR2019/051392, filed on Jun. 7, 2019, which claims priority to French Patent Application No. 1855222, filed on Jun. 14, 2018.

BACKGROUND OF THE INVENTION

The present disclosure relates to the field of aeronautical propulsion, and more particularly to an emptying and monitoring device for emptying and monitoring a fluid drained from an aircraft engine.

In the present context, what is meant by an "aircraft engine" is any propulsor carried on-board an aircraft and intended for its flight propulsion, in particular gas turbine engines such as for example turbojets, turbofans, turboprops or turboshafts, but also piston engines or electric motors.

Normally, aircraft engines comprise moving parts subjected to high mechanical and thermal stresses. It is therefore generally important to supply with lubricating fluid certain elements of the engine, particularly rotating shaft support bearings. In addition, aircraft engines can also comprise hydraulic actuators, which can in particular use fuel as a hydraulic fluid and/or as a lubricant. A portion of these fluids can escape by evaporation or liquid flow, and represents a potential source of environmental pollution. Thus, to reduce or avoid this pollution, on-board reservoirs have been proposed, in particular in the publication of the international patent application WO 2015/082833 A1, for receiving fluids drained from the engine, and contain them until their supervised emptying.

In addition, in order to monitor the condition of an engine, and particularly of its lubricating fluid, it is known to proceed with analyses of this lubricating fluid. However, this usually requires the collection of samples of the lubricating fluid of the engine, and their transport to an analysis device, which can be difficult when this engine is carried on-board an aircraft.

Finally, it is also known to integrate lubricating fluid quality sensors directly into the lubrication circuit of an aircraft. However, this integration can be difficult due to the necessity of maintaining the circulation of the lubricating fluid through this circuit.

OBJECT AND SUMMARY OF THE INVENTION

The present disclosure aims to remedy these drawbacks, by proposing an emptying and monitoring device for emptying and monitoring a fluid drained from an aircraft engine, which allows a more immediate analysis of this fluid in order to contribute to the monitoring of the engine.

According to a first aspect, this aim can be achieved thanks to the fact that the emptying and monitoring device comprises a first intake passage for receiving the fluid drained from the engine directly from the aircraft, and in that the emptying and monitoring device also comprises a quality sensor assembly for detecting at least one quality parameter of the fluid drained from the engine admitted through the first intake passage. This quality sensor assembly can in particular comprise a viscosity sensor for detecting a viscosity of the fluid drained from the engine and/or a pollutant sensor assembly for detecting a presence of pollutants in the fluid drained from the engine. More particularly, this pollutant sensor assembly can comprise an electrical conductivity sensor, a ferromagnetic particle sensor, an optical sensor and/or an acoustical sensor. The electrical conductivity sensor can in particular be configured to contribute to the detection of water and/or other pollutants in the fluid drained from the engine, while the optical or acoustic sensor can be configured to carry out a measurement of transmission, absorption, reflection and/or refraction of the fluid contained in the on-board reservoir, over one or more wavelengths, particularly in order to characterize the composition, decantation and/or stratification of the fluid drained from the engine.

Thanks to the direct reception from the aircraft of the fluid drained from the engine and to the installation of the quality sensor assembly in the emptying and monitoring device, it is thus possible to contribute immediately to a monitoring of the condition of the engine during the emptying of this fluid, which can in particular have been received and stored in an on-board reservoir before its emptying, and particularly but not solely to a monitoring of the condition of its lubricating fluid, at least by means of the quality of the fluid drained naturally from the engine, this therefore without having to interfere in the normal circulation of the operating fluids within the engine. In addition, the analyzed fluid not necessarily being filtered, it can be richer in information.

In addition, the emptying and monitoring device can further include a first reservoir, connected to the first intake passage, with a first level sensor to detect a level of fluid in the first reservoir. Thus, it is possible to monitor, not only the quality of the drained fluid, but also its quantity, thus allowing the identification of possible blockages and/or leaks in its circulation within the engine.

According to a first alternative, the first intake passage can be configured to establish a leak-tight connection with an emptying passage disposed on the aircraft. In particular, the first intake passage can be extensible for this connection with the emptying passage on the aircraft. It can in particular be incorporated in a telescopic and/or articulated pole or arm. Thus, it is possible to minimize or eliminate any external pollution during the emptying of the drained fluid to the emptying and monitoring device.

However, according to a second alternative, the first intake passage can comprise a basin for receiving by gravity the fluid drained from the engine so as to facilitate the emptying by simply allowing the fluid to flow by gravity from an emptying passage located on the aircraft toward this reception basin and open for this emptying.

The emptying and monitoring device can further comprise, downstream of the first quality sensor assembly, at least one treatment device, for treating the fluid drained from the engine having been admitted through the first intake passage. In this context, the term "downstream" should be understood with respect to a circulation direction, through the emptying and monitoring device, of the fluid drained from the engine and having been admitted through the first intake passage. The at least one treatment device can comprise, for example, a centrifuge and/or a decantation tank to allow at least a partial separation of the components of the fluid drained from the engine and thus ensure its environmentally responsible treatment, for example by facilitating its recycling.

The emptying and monitoring can thus comprise at least one second intake passage for receiving, directly from the aircraft, fluid drained from the engine, and a second quality sensor assembly for detecting at least one quality parameter of the fluid drained from the engine having been admitted through the second intake passage. It can thus be possible to separately detect quality parameters of fluid drained from different areas of the engine, thus facilitating its monitoring and more precise diagnostic.

A second aspect of this disclosure relates to an airport service vehicle comprising the emptying and monitoring device mentioned above. In addition, this airport service vehicle can comprise an autonomous control system. Thus, the airport service vehicle can move the emptying and monitoring device to the aircraft when stopped or even in motion over the runways of an airport to carry out emptying and an immediate analysis of the fluid drained from the engine.

Alternatively, however, according to a third aspect, this disclosure also relates to a fixed airport service installation comprising the emptying and monitoring device mentioned above.

A fourth aspect of this disclosure relates to an emptying and monitoring method for emptying and monitoring a fluid drained from an aircraft engine, the emptying and monitoring method being able to comprise an admission step, through a first intake passage of an emptying and monitoring device, of fluid drained from the aircraft engine, directly from the aircraft, and a step of detecting, by means of a quality sensor assembly, of at least one quality parameter of the fluid drained from the aircraft engine having been admitted through the first intake passage. This method can further comprise a prior step of moving the emptying and monitoring device, on-board an airport service vehicle, to the aircraft, and in particular autonomous control of the vehicle during this movement step.

Moreover, this method can further comprise a step of connecting the first intake passage with an emptying passage on the aircraft, which can in particular be accomplished automatically.

Alternatively, however, the method can comprise a step of emptying by gravity the fluid drained from an aircraft engine, directly from the aircraft into a reception basin of the intake passage.

BRIEF DESCRIPTION OF THE DRAWINGS

The invention will be well understood and its advantages will appear more clearly upon reading the detailed description that follows, of embodiments shown by way of non-limiting examples. The description refers to the appended drawings in which:

FIG. 4 illustrates schematically an airport service vehicle equipped with an emptying and monitoring device according to a second embodiment of the invention, and FIG. 5 illustrates schematically an aircraft in a fixed airport service installation equipped with an emptying and monitoring device according to a third embodiment of the invention.

DETAILED DESCRIPTION OF THE INVENTION

Figure 1:
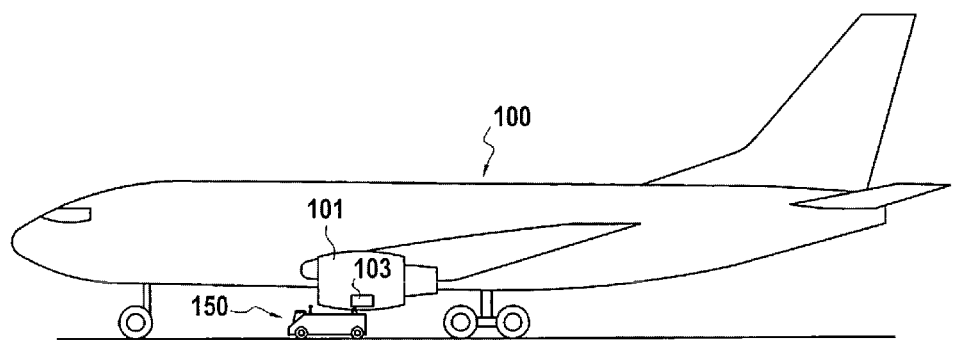
FIG. 1 illustrates schematically an aircraft connected to an airport service vehicle equipped with an emptying and monitoring device according to a first embodiment of the invention.

As illustrated in FIG. 1, an aircraft 100 can comprise, for example below the engine 101 in a nacelle surrounding the engine 101, an on-board reservoir 103 for receiving fluid drained from the engine 101, particularly in flight. An emptying and monitoring device 10 according to a first embodiment can be installed on-board an airport service vehicle 150 for moving it to an aircraft 100 in order to proceed with the emptying of a fluid drained from an engine 101 of the aircraft 100.

Figure 2:
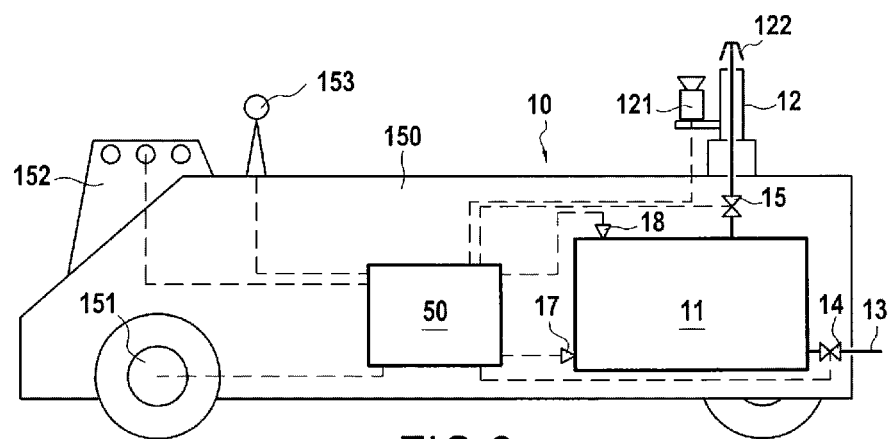
FIG. 2 illustrates schematically in greater detail the airport service vehicle of FIG. 1.

As illustrated in greater detail in FIG. 2, this emptying and monitoring device 10 can comprise a first intake passage 12 with a valve 15, a first reservoir 11 connected to this first intake passage 12, a passage 13 for emptying the first reservoir 11 with a valve 14, a first quality sensor assembly 17 and a first level sensor 18, installed in the first reservoir 11.

The first intake passage 12 can be configured to receive, directly from the aircraft 100, and more particularly from an emptying passage of the on-board reservoir 103, the fluid drained from the engine 101. To this end, this intake passage 12 can be extensible and configured to establish a leak-tight connection with the emptying passage of the on-board reservoir 103. Thus, as illustrated, the first intake passage 12 can for example be formed in an articulated and/or telescoping pole similar to those used for in-flight refueling, possibly equipped with a camera 121, or with another sensor, for guiding it to the emptying passage of the on-board reservoir 103, and with a connector 122, which can in particular be a male connector for the leak-tight connection with the emptying passage of the on-board reservoir 103. The valve 15 can allow the blocking of the intake passage 12 when it is not used for emptying the fluid drained from an aircraft engine, so as to avoid the contamination of the reservoir 11 with other substances.

The first reservoir 11 can be configured to contain, at least temporarily, the fluid received from the aircraft 100 and admitted through the first intake passage 12, so as to allow the quality sensor assembly 17 to detect at least one quality parameter of the fluid drained from the engine 101, admitted into the emptying and monitoring device 10 through the first intake passage 12, and contained in the first reservoir 11, and the first level sensor 18 to detect the volume of fluid emptied from the aircraft 101 through the first intake passage 12. The quality sensor assembly 17 can in particular comprise a sensor for the viscosity of the fluid drained from the engine and/or an assembly for sensing pollutants present in the fluid drained from the engine. The pollutant sensor assembly can in particular comprise at least one ferromagnetic particle sensor, an electrical conductivity sensor, an optical sensor and/or an acoustic sensor. The viscosity sensor and the ferromagnetic particle sensor can be located outside the first reservoir 11 and in particular upstream of it, as for example in the first intake passage 12, in contact with the dynamic flow of the fluid. It is however also conceivable to install them in the first reservoir 11, or in a duct appended to it. The optical or acoustic sensor can be configured to carry out a measurement of the transmission, absorption, reflection and/or refraction of the fluid contained in the on-board reservoir, at one or more wavelengths, particularly in order to characterize the composition, decantation and/or stratification of this fluid in the on-board reservoir.

The first level sensor 18 and the first quality sensor assembly 17 can be connected to the control unit 50. The control unit 50 can be configured to determine, from the data detected by the first level sensor 18 and by the first quality sensor assembly 17, not only the quantity of fluid drained from the engine 101, but also its physical and/or chemical qualities, and in particular its suspended pollutant content, including water and/or particles. Moreover, the control unit 50 can comprises an integrated memory for storing these data and be integrated into and/or connected to a prognosis and health management (or PHM) system of the engine 101, carried on-board the aircraft 100 and/or located on the ground, allowing a diagnostic of the engine 101 to be performed to direct its predictive maintenance depending on the quantity of fluid drained from the engine 101 and its physical and/or chemical characteristics, as determined by the control unit 50 based on the data detected by the level sensor 18 and by the first quality sensor assembly 17, alone or in combination with other factors. The prognosis and health management system can in particular be configured to diagnose a seal failure within the engine 101 and/or excessive wear of moving parts of the engine 101, and possibly recommend a maintenance or inspection operation, immediate or deferred, and/or allow the takeoff of the aircraft 100 depending on this diagnosis.

The emptying passage 13 of the emptying and monitoring device 10 can be configured to allow the emptying of the reservoir 11 by opening the valve 14, so as to free its capacity to proceed with the emptying and analysis of the fluid drained from other engines and/or other aircraft. As illustrated the valves 14 and 15 and/or the pole forming the intake passage 12 can also be connected to a control unit 50, which can therefore be configured to control the guidance of the pole and its connection to the emptying passage of the on-board reservoir 103 and/or the opening and closing of the valves 14 and 15.

As illustrated in FIG. 2, the airport service vehicle 150 can also comprise sensors 152, for example optical and/or radar sensors, a wireless communication terminal 153 and a propulsion, steering and braking device 151, connected to the control unit 50 to form an autonomous control device allowing controlling the movement of the airport service vehicle 150, with the emptying and monitoring device 10, through the airport service installations and to the aircraft.

Figure 3:
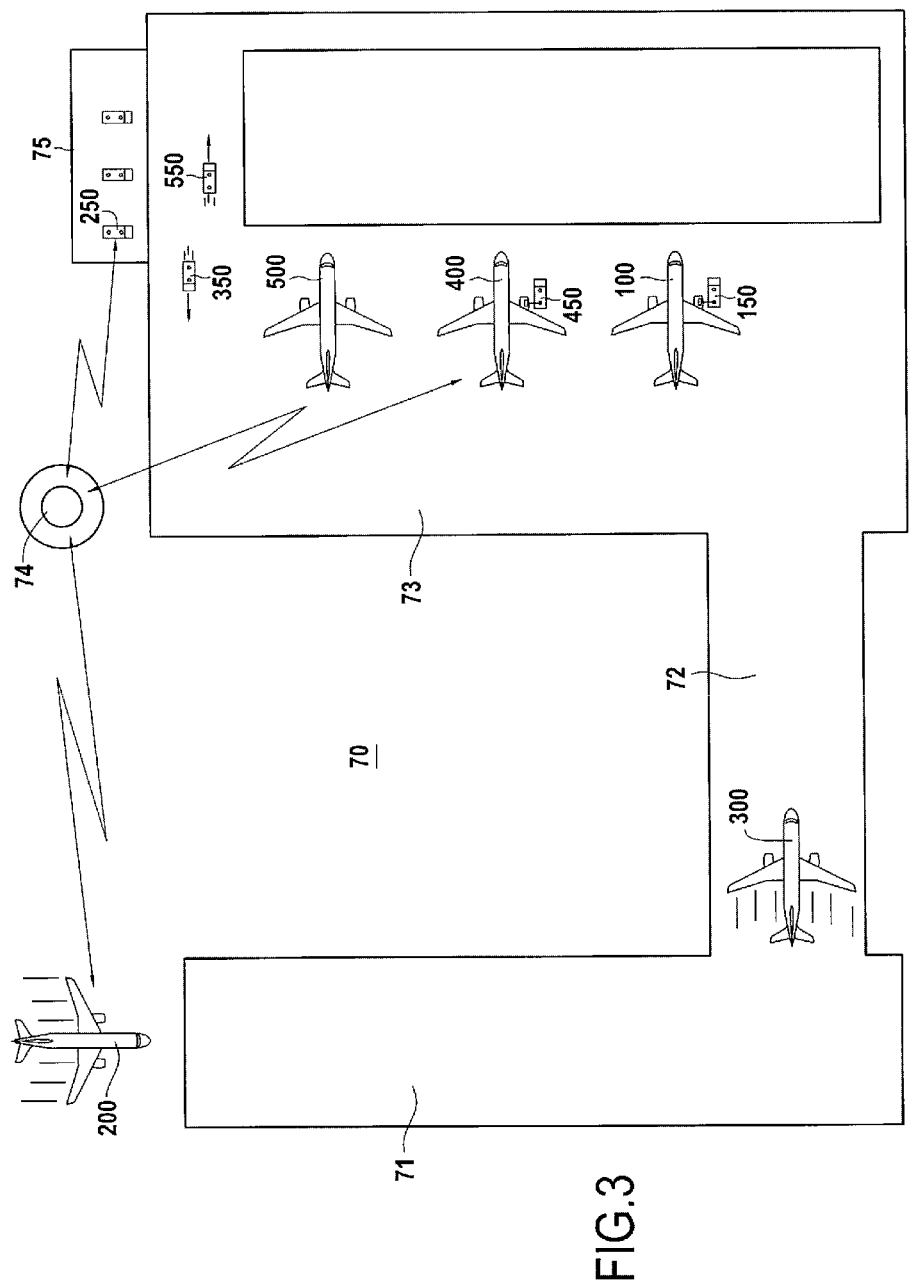
FIG. 3 illustrates schematically the organization of an airport equipped with several airport service vehicles like that of FIGS. 1 and 2.

In operation, an airport service vehicle with these autonomous control and emptying and monitoring devices can follow a method like that illustrated in FIG. 3, in which the aircraft 200, 300, 400 and 500 are aircraft similar to the aircraft 100 and including equivalent elements, and the airport service vehicles 250, 450 and 550 are airport service vehicles similar to the airport service vehicle 150 and also including equivalent elements. Already on approach to the landing runway 71 of the airport 70, the aircraft 200 can transmit a signal to a communication center, for example to the control tower 74. As a result of this signal, the corresponding airport service vehicle 250, parked in a first parking zone 75, can be activated and receive instruction to move to a location, on a second parking zone 73, designated for the aircraft 200 on approach, in order to proceed with its emptying. Thus, while another aircraft 300, having already landed, is moving on a taxiway 72 toward its designated location on the second parking zone 73, the corresponding airport service vehicle 350 can already be moving, controlled autonomously from the first parking zone 75 to meet it at this designated location.

At the designated location for the aircraft 100, or even when it is still moving on the taxiway 72 toward the second traffic zone, the corresponding airport service vehicle 150 can proceed to deploy automatically toward the aircraft 100 the articulated and/or telescoping pole forming the intake passage 12 of its emptying and monitoring device 10, possibly guided by the control unit 50 with images detected by the camera 121, until it connects the intake passage 12 of its emptying and monitoring device 10 to the emptying passage of the on-board reservoir 102 on the aircraft 100, as already illustrated in FIG. 1. After this connection, which can be a leak-tight connection to reduce the risk of environmental pollution, the control unit 50 can command the opening of the valve 15 to proceed with the admission, directly from the aircraft 100 by the first intake passage 12, of the fluid drained from the engine 101 and contained in the on-board reservoir 103. This fluid is thus admitted into the emptying and monitoring device 10 on-board the airport service vehicle 150, where it is possible to proceed with the detection, through the quality sensor assembly 17, of at least one quality parameter of the fluid, as well as its volume by means of the level sensor 18. These data can be transmitted by the quality sensor assembly 17 and by the level sensor 18 to the control unit 50 to determine physical and/or chemical characteristics of the fluid, and in particular its content of suspended pollutants, including water and/or particles. This information can then be transmitted to the prognosis and health management system, allowing the direction of its predictive maintenance.

Thus for example, the data detected by the first quality sensor assembly 17 can allow identifying the proportions of lubricant, fuel and water in the fluid drained from the engine 101. The control unit 50, by multiplying these proportions by the total volume of drained fluid, which can be deduced from the data detected by the first level sensor 18, can obtain the total volumes of lubricant, fuel and water drained from the engine 101 to the first compartment 11. A seal failure of the lubricated portions of the engine 101, which in particular can affect the quality of the air collected from the engine 101 for the cabin pressurization system of the aircraft 100, can be diagnosed by the prognosis and health management system as a result of the detection of an excessive volume of lubricant in the drained fluid. The detection of an excessive volume of fuel in the drained fluid, on the other hand, can allow the prognosis and health management system to diagnose a seal failure of the fuel supply circuit and/or actuators using fuel as a hydraulic fluid. The data detected by the first quality sensor assembly 17 can allow identifying the quantity and type of solid particles in the fluid drained from the engine 101 to the first compartment 11, distinguishing in particular between ferromagnetic particles and particles rich in carbon. The prognosis and health management system can thus diagnose excessive wear upon detecting, by the first quality sensor assembly 17, an excessive quantity of ferromagnetic particles in this drained fluid, in particular ferromagnetic particles of a size exceeding a predetermined threshold, while poor combustion within a combustion chamber of the engine 101 could be diagnosed by the prognosis and health management system as a result of the detection of an excessive quantity of particles rich in carbon in this same drained fluid. As a result of these diagnostics, the prognosis and health management system can also recommend a maintenance or inspection operation, immediate or deferred, and/or allow the takeoff of the aircraft 100 depending on this diagnostic.

After the emptying of the on-board reservoir having been completed, as in the case of the aircraft 400 in FIG. 3, the corresponding airport service vehicle 450 can proceed to withdraw its pole and transmit a task completion signal, to then return, also autonomously, to the first parking zone 75, like the airport service vehicle 550 returning from the location of the corresponding aircraft 500. Having returned to the first parking zone 75, or into another designated location for the emptying of the reservoir 11, the control unit 50 can command the opening of the valve 14 of the emptying passage 13 of the emptying and monitoring device 10, to thus eliminate the fluids drained from the engine 101 in a supervised and environmentally responsible manner.

Even if, in the embodiment illustrated in FIGS. 1 and 2, the emptying and monitoring device includes only a single intake passage, it is also conceivable that it includes a plurality of distinct intake passages, allowing in particular the separate admission of fluids drained from different areas of the engine 101 and contained in separate compartments in the on-board reservoir 103, or even in a plurality of distinct on-board reservoirs 103, with respective emptying passages. A quality sensor assembly can be associated with each intake passage, to thus proceed separately with the analysis of fluids drained from each different area of the engine 101, in order to ensure a more precise monitoring and diagnostic. In addition, the emptying and monitoring device can comprise, downstream of one or more quality sensor assemblies, at least one device for treating the fluid drained from the engine 101 to facilitate the environmentally responsible elimination of this fluid.

Thus, as illustrated in FIG. 4, the emptying and monitoring device 10 can comprise not only a first intake passage 12 with a valve 15, a first reservoir 11 connected to this first intake passage 12, an emptying passage 13 of the first reservoir 11 with a valve 14, a first quality sensor assembly 17 and a first level sensor 18, installed in the first reservoir 11, but also a second intake passage 22 with a valve 25, a second reservoir 21 connected to this second intake passage 22, an emptying passage 23 of the second reservoir 21 with a valve 24, a second quality sensor assembly 27 and a second level sensor 28, installed in the second reservoir 21. Each of the first and second intake passages 12, 22, reservoirs 11, 21, quality sensor assemblies 17, 27, level sensors 18, 28, and emptying passages 15, 25 can be respectively equivalent to the first intake passage 12, reservoir 11, quality sensor assembly 17, level sensor 18, and emptying passage 15 of the emptying and monitoring device 10 illustrated in FIG. 2, and operate similarly. Thus, as illustrated, the first intake passage 12 can also be formed in an articulated and/or telescoping pole similar to those use fused for in-flight refueling, possibly equipped with a camera 221, or with another sensor, connected to the control unit 50, for its guidance toward a second emptying passage of the on-board reservoir 103, and a connector 222, which can in particular be a male connector, for the leak-tight connection with this second emptying passage of the on-board reservoir 103.

Thus the first and second level sensors 18, 28 and the first and second quality sensor assemblies 17, 27 can be connected to the control unit 50, which can be configured to determined individually, from the data detected by them, the quantity and the physical and/or chemical characteristics of the fluid drained from the engine 101, having been admitted through each intake passage 12, 22. Aside from that, the control unit 50 can be equivalent to that of the device illustrated in FIG. 2, and operate similarly.

As also illustrated in FIG. 4, the emptying and monitoring device 10 can also comprise, downstream of the emptying passages 13, 23, a treatment device 31, which can in particular be a centrifuge or a decantation tank, with its own emptying passage 33 equipped with its own valve 34. As illustrated, the valve 34 can also be connected to the control unit 50. Thus, between the emptying of the reservoirs 11, 21 by opening of the valves 14, 24 commanded by the control unit 50, and that of the treatment device 31 by opening of the valve 34, this treatment device 31 can proceed with a treatment of the fluid originating in the reservoirs 11, 21, to then thus facilitate its elimination in an environmentally responsible manner at a location designated for the emptying of the treatment device 31. The remaining elements of the emptying and monitoring device 10 and of the airport service vehicle 150 according to FIG. 4 are equivalent to those of FIG. 2 and therefore receive the same reference symbols.

Although, in the first and second embodiments illustrated, the emptying and monitoring device 10 is integrated into an airport service vehicle, it is also conceivable to integrate it into a fixed airport service installation, as illustrated in FIG. 5. Thus, as illustrated, the reservoir 11 can be buried under the tarmac of the airport, and the intake passage 12 comprise a basin 123 in the surface of the tarmac, disposed to receive the fluid drained from the engine 101 of an aircraft 100 disposed at an appropriate emptying station. This emptying station can, for example, be situated in a taxiway or in an aircraft parking zone. As illustrated, the emptying and monitoring device 10 can comprise a surface-mounted station 60, connected to the control unit 50, and able to establish a wireless connection with an on-board terminal 106 on-board the aircraft 100. This on-board terminal 106 can be connected, in turn, to the emptying passage 104 of the on-board reservoir 103, to control its opening and/or closing. The remaining features of the emptying and monitoring device 10 according to this embodiment can be similar to those of that illustrated in FIG. 2, and receive the same reference symbols.

Thus, the aircraft 100 can be directed to this emptying station. The on-board terminal 106 can establish a wireless communication with the station 60 and, when it is established that the emptying passage 104 is located directly facing the basing 123, the fluid drained from the engine 101 and contained in the on-board reservoir 103 can thus be emptied and flow naturally by gravity from the on-board reservoir 103 to the reservoir 11 of the emptying and monitoring device 10, passing through the emptying passage 104 and the basin 123 and the intake passage 12. After this emptying is complete, the on-board terminal 106 and the control unit 50 can command, respectively, the closure of the emptying passage 104 of the on-board reservoir 103 and that of the intake passage 12 of the emptying and monitoring device 10, and the aircraft 100 can possibly leave this emptying station while it is possible to proceed, in the reservoir 11, with the detection, by means of the quality sensor assembly 17, of at least one quality parameter of the fluid, as well as its volume, by means of the level sensor 18. These data can be transmitted by the quality sensor assembly 17 and by the level sensor 18 to the control unit 50 to monitor in this manner the condition of the engine 101, possibly within the scope of a prognosis and health management system allowing directing its predictive maintenance. After the detection of these parameters, the control unit 50 can again proceed with commanding the opening of the valve 14 of the emptying passage 13 of the emptying and monitoring device 10, to thus remove the fluids drained from the engine 101 in a controlled and environmentally responsible manner.

Although the present invention has been described by referring to specific exemplary embodiments, it is obvious that different modifications and changes can be performed on these examples without departing from the general scope of the invention as defined by the claims. In addition, individual features of the different embodiments mentioned can be combined into additional embodiments. Thus, for example, the airport service vehicle according to the first embodiment could be equipped with a reception basin for the fluid drained from the aircraft, rather than an extensible pole. Conversely, the airport service installation of the third embodiment could be equipped with an extensible pole, rather than a basin, or with a plurality of distinct intake passages and quality sensor assemblies for the separate admission and analysis of fluid originating from several different portions of the engine. Consequently, the description and the drawing must be considered in an illustrative, rather than a restrictive sense.

The invention claimed is:

1. An emptying and monitoring device for emptying an on-board reservoir of a fluid drained from an engine of an aircraft and for monitoring the fluid drained from the engine of the aircraft, the emptying and monitoring device comprising:
   an articulated pole incorporating an extensible first intake passage configured to establish a leak-tight connection with an emptying passage disposed on the aircraft for receiving, directly from the aircraft, the fluid drained from the engine, and
   a first quality sensor assembly for detecting at least one quality parameter of the fluid drained from the engine having been admitted through the first intake passage.

2. The emptying and monitoring device according to claim 1, wherein the first quality sensor assembly comprises a viscosity sensor for detecting a viscosity of the fluid drained from the engine.

3. The emptying and monitoring device according to claim 1, wherein the first quality sensor assembly comprises a pollutant sensor assembly for detecting a presence of pollutants in the fluid drained from the engine.

4. The emptying and monitoring device according to claim 1, further comprising, downstream of the first quality sensor assembly, at least one treatment device for treating the fluid drained from the engine having been admitted through the first intake passage.

5. The emptying and monitoring device according to claim 1, further comprising:
   a second intake passage for receiving, directly from the aircraft, fluid drained from the engine, and
   a second quality sensor assembly for detecting at least one quality parameter of the fluid drained from the engine having been admitted through the second intake passage.

6. Fixed airport service installation comprising the emptying and monitoring device according to claim 1.

7. The emptying and monitoring device according to claim 1, wherein the articulated pole is also telescopic.

8. An airport service vehicle comprising the emptying and monitoring device according to claim 1.

9. The airport service vehicle according to claim 8, comprising an autonomous control device.

10. An emptying and monitoring method for emptying an on-board reservoir of a fluid drained from an engine of an aircraft and monitoring the fluid drained from the engine of the aircraft, the emptying and monitoring method comprising the following steps:
    connecting, in a leak-tight manner, an extensible first intake passage, incorporated in an articulated of an emptying and monitoring device,
    admitting, through the first intake, of fluid drained from the engine of the aircraft directly from the aircraft, and
    detecting, by means of a first quality sensor assembly in the emptying and monitoring device, of at least one quality parameter of the fluid drained from the engine of the aircraft having been admitted through the first intake passage.

11. The emptying and monitoring method according to claim 10, wherein the connecting step is accomplished automatically.

12. The emptying and monitoring method according to claim 10, wherein the articulated pole is also telescopic.

13. The emptying and monitoring method according to claim 10, further comprising a step of moving the emptying and monitoring device, on-board an airport service vehicle, to the aircraft.

14. The emptying and monitoring method according to claim 13, comprising autonomous control of the airport service vehicle during the movement step.

* * * * *